US008473246B1

(12) United States Patent
Thorn et al.

(10) Patent No.: US 8,473,246 B1
(45) Date of Patent: Jun. 25, 2013

(54) CABLE MEASUREMENT DEVICE

(75) Inventors: Stuart W. Thorn, Chattanooga, TN (US); Venkata Kiran Manchiraju, Villa Rica, GA (US)

(73) Assignee: Southwire Company, Carrollton, GA (US)

( * ) Notice: Subject to any disclaimer, the term of this patent is extended or adjusted under 35 U.S.C. 154(b) by 587 days.

(21) Appl. No.: 12/613,645

(22) Filed: Nov. 6, 2009

Related U.S. Application Data

(60) Provisional application No. 61/111,864, filed on Nov. 6, 2008.

(51) Int. Cl.
*G01B 5/02* (2006.01)
*G01R 27/04* (2006.01)

(52) U.S. Cl.
USPC .......................................... 702/159; 324/644

(58) Field of Classification Search
USPC ............. 702/159, 57, 66–68, 79, 81, 84, 127, 702/149, 155, 158, 182–183, 189; 324/76.11, 324/527, 533–535, 600, 602–603, 605, 609, 324/637, 639, 642, 644; 356/450, 457, 482, 356/486, 496, 498, 625, 634; 33/700–701
See application file for complete search history.

(56) References Cited

U.S. PATENT DOCUMENTS

| 3,857,091 | A | 12/1974 | Kalifon | 324/52 |
| 4,680,574 | A | 7/1987 | Ruffner | 340/571 |
| 6,277,084 | B1 | 8/2001 | Abele et al. | 601/2 |
| 6,646,451 | B2 | 11/2003 | Lanan | 324/642 |
| 6,771,076 | B1* | 8/2004 | Smith | 324/533 |
| 7,098,645 | B1 | 8/2006 | Zhu et al. | 324/76.11 |
| 7,116,760 | B2 | 10/2006 | Smith et al. | 379/22.02 |
| 7,135,873 | B2 | 11/2006 | McCosh | 324/644 |
| 7,245,129 | B2 | 7/2007 | Wajcer et al. | 324/533 |
| 2001/0020663 | A1* | 9/2001 | Petersen et al. | 242/485.7 |
| 2002/0130668 | A1 | 9/2002 | Blades | 324/536 |
| 2003/0201780 | A1 | 10/2003 | Blades | 324/523 |
| 2008/0030202 | A1 | 2/2008 | Wang | 324/533 |

OTHER PUBLICATIONS

Hartmann et al., Problems in the Acoustic Determination of the Modulus of Fibers, Jul. 31, 1972, Naval Ordnance Laboratory, White Oak, Silver Spring, Maryland, NOLTR 72-149, 25 pp.*

* cited by examiner

*Primary Examiner* — Toan Le
(74) *Attorney, Agent, or Firm* — Merchant & Gould

(57) ABSTRACT

A length of a cable may be measured. First, a wave may be transmitted in a cable. Then, the transmitted wave may be received. Next, a length of the cable between a first end of the cable and a second end of the cable may be calculated based upon a time the transmitted wave took to travel in the cable.

16 Claims, 4 Drawing Sheets

CABLE MEASUREMENT DEVICE

RELATED APPLICATION

Under provisions of 35 U.S.C. §119(e), Applicant claims the benefit of U.S. provisional application No. 61/111,864, filed Nov. 6, 2008, which is incorporated herein by reference.

COPYRIGHTS

All rights, including copyrights, in the material included herein are vested in and the property of the Applicants. The Applicants retain and reserve all rights in the material included herein, and grant permission to reproduce the material only in connection with reproduction of the granted patent and for no other purpose.

BACKGROUND

Electrical energy is transmitted using power lines. Power lines include electrical conductors configured to conduct the electrical energy. The electrical conductor may be wound onto a cable reel in order to be sold or transported. Determining how long a conductor is, especially when it is on a cable reel, is difficult. This problem may be complicated when a portion of the cable on the reel is cut off and used, thus leaving an unknown amount of the cable on the reel. Also, since the cable may be sold by length, knowing the length of a cable on a reel can help determine cost for the reel of cable.

SUMMARY

This Summary is provided to introduce a selection of concepts in a simplified form that are further described below in the Detailed Description. This Summary is not intended to identify key features or essential features of the claimed subject matter. Nor is this Summary intended to be used to limit the claimed subject matter's scope.

A length of a cable may be measured. First, a wave may be transmitted in a cable. Then, the transmitted wave may be received. Next, a length of the cable between a first end of the cable and a second end of the cable may be calculated based upon a time the transmitted wave took to travel within the cable.

Both the foregoing general description and the following detailed description provide examples and are explanatory only. Accordingly, the foregoing general description and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present invention. In the drawings.

DETAILED DESCRIPTION

Figure 1:
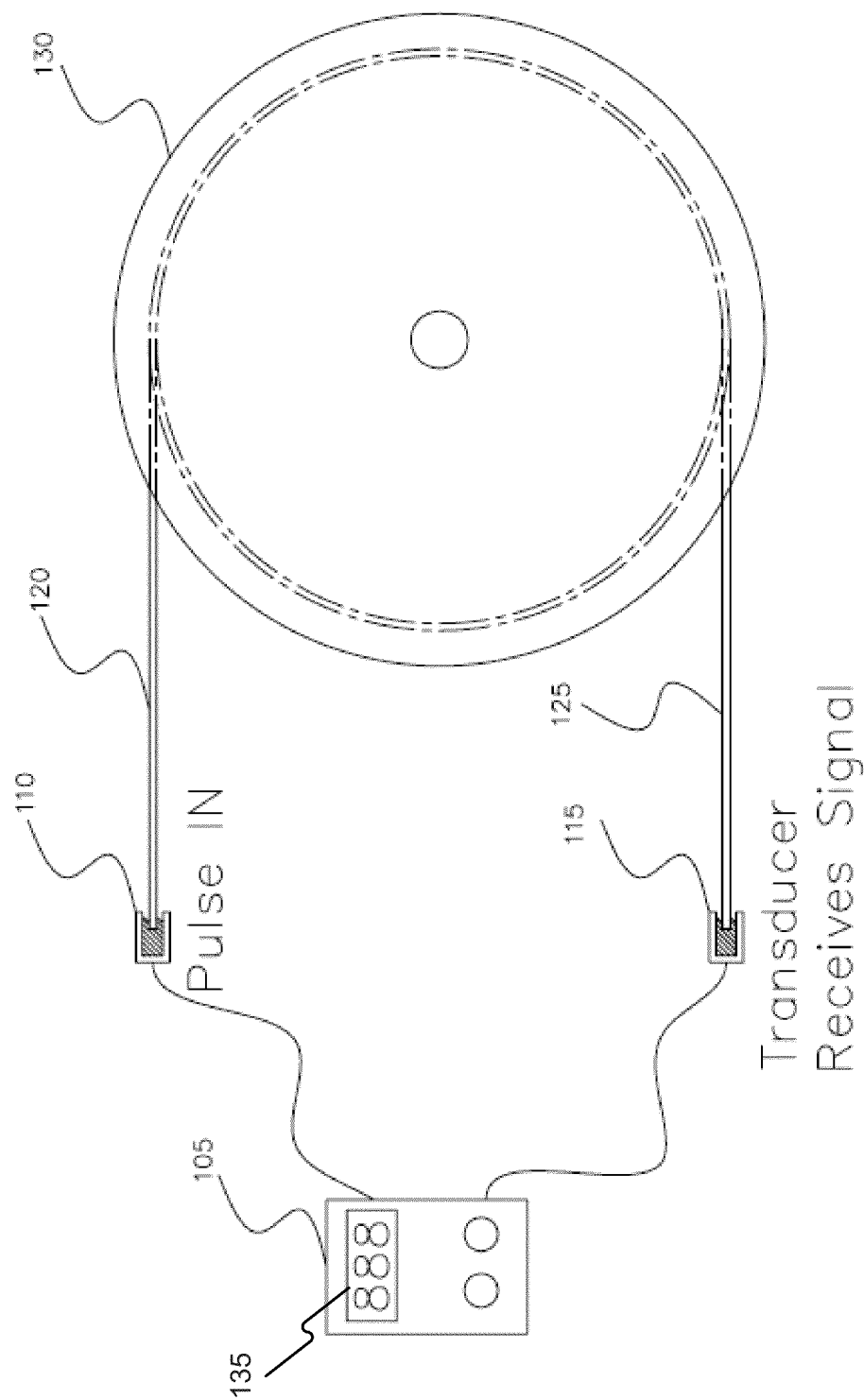
FIG. 1 shows a cable measurement device configured to send a signal at one end of a cable and receive the signal at another end of the cable.

The following detailed description refers to the accompanying drawings. Wherever possible, the same reference numbers are used in the drawings and the following description to refer to the same or similar elements. While embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention.

Consistent with embodiments of the invention, a cable measurement device may be provided. The cable measurement device may use ultrasonic propagation to accurately measure a cable's length. Ultrasonic waves may comprise elastic waves and may be propagated through a solid or liquid material. Consistent with embodiments of the invention, the cable measurement device may accurately measure a time for a signal (e.g. an ultrasonic signal) to travel the cable's length. For example, the cable measurement device may generate an elastic wave (e.g. using a vibrating member) at one end of the cable with a transmitter. At another end of the cable, the cable measurement device may provide a receiver to detect the generated vibration. The cable measurement device may then perform a velocity calculation on the vibration to determine the cable's length.

Consistent with other embodiments of the invention, the cable measurement device may combine the aforementioned transmitter with the aforementioned receiver to from a transceiver. Consequently, the cable measurement device may vibrate the cable to produce an ultrasonic wave in the cable and measure a reflected wave at a point at or near where the ultrasonic wave was generated. The cable measurement device may then perform a velocity calculation on the vibration to determine the cable's length.

The cable may comprise any type cable capable of transmitting electrical energy. For example, the cable may comprise, but is not limited to, aluminum conductor steel reinforced (ACSR), all aluminum conductor (AAC), all aluminum alloy conductor (AAAC), medium voltage direct bury cable, high voltage direct bury cable, secondary duplex, secondary triplex, etc. Consequently, the aforementioned velocity calculation may be based on the conductor type. For example, the velocity calculation may take into consideration different parameters when calculating the length of ACSR as compared to AAC. The cable measurement device may include a user interface so that an operator may enter the type of conductor the cable measurement device is measuring. Accordingly, the cable measurement device may calculate the length based on the conductor type that was input in the user interface.

Embodiments of the invention may use various processes to measure the vibration velocity. These processes may comprise, but are not limited to, laser interferometers, holographic interferometers, and fiber optics. The aforementioned processes may overcome any issues created by dissipation in energy of the signal in the cable. This energy dissipation may be due to, for example, scattering, and absorption differences in elastic properties of the medium (e.g. cable.) Consistent with embodiments of the invention, the frequency/wavelength of the signal (e.g. ultrasonic wave) may be optimized to material properties of the cable to minimize attenuation. Moreover embodiments of the invention may include sensors (e.g. transmitters, receivers, or transceivers) configured to maximize cable length measurement accuracy.

FIG. 1 shows a cable measurement device 105. Cable measurement device 105 may be used in a cable measurement process. Consistent with embodiments of the invention, cable measurement device 105 may be configured to use a transmitter 110 to transmit a first signal onto a first end 120 of a cable. Cable measurement device 105 may be further configured to use a receiver 115 to receive the first signal at a second end 125 of the cable. The cable may be wound on a cable reel 130 during the cable measurement process. The first signal may comprise, for example, an elastic wave such as an ultrasonic wave. After the first signal is transmitted and received, cable measurement device 105 may then calculate a length of the cable between first end 120 and second end 125. The length may be calculated based upon a time the first signal took to travel between first end 120 of the cable and second end 125 of the cable. The calculated length may then be displayed on a display 135 on cable measurement device 105. The aforementioned length calculation process may be performed by cable measurement device 105 while the cable is on reel 130.

Figure 2:
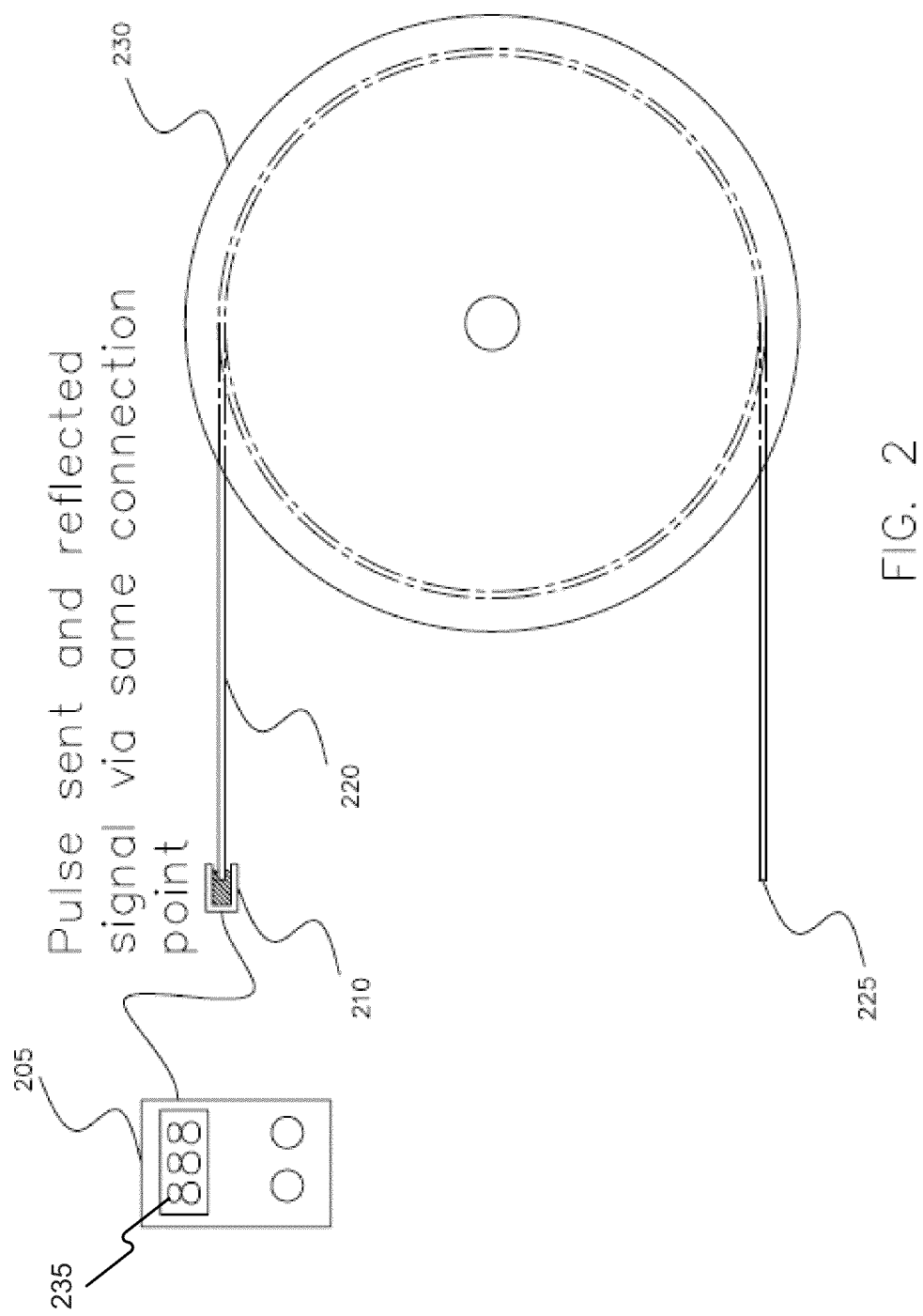
FIG. 2 shows a cable measurement device configured to send a signal at one end of a cable and receive the signal at the same end at which the signal was sent.

FIG. 2 shows a cable measurement device 205. Cable measurement device 205 may be used in a cable measurement process. Consistent with embodiments of the invention, cable measurement device 205 may be configured to use a transceiver 210 to transmit a second signal onto a first end 220 of a cable. Cable measurement device 205 may be further configured to use transceiver 210 to receive a reflected version of the second signal at first end 220 of the cable. Once transmitted onto the cable, the second signal may hit a second end 225 of the cable and be reflected back to first end 220 from second end 225 of the cable. The cable may be wound on a cable reel 230 during the cable measurement process. Like the first signal, the second signal may comprise an elastic wave such as an ultrasonic wave. After the second signal is transmitted and received, cable measurement device 205 may then calculate a length of the cable between first end 220 and second end 225. The length may be calculated based upon a time the second signal took to travel from first end 220, hit second end 225, and reflect back to first end 220. The calculated length may then be displayed on a display 235 on cable measurement device 205. The aforementioned length calculation process may be performed by cable measurement device 205 while the cable is on reel 230.

Figure 3:
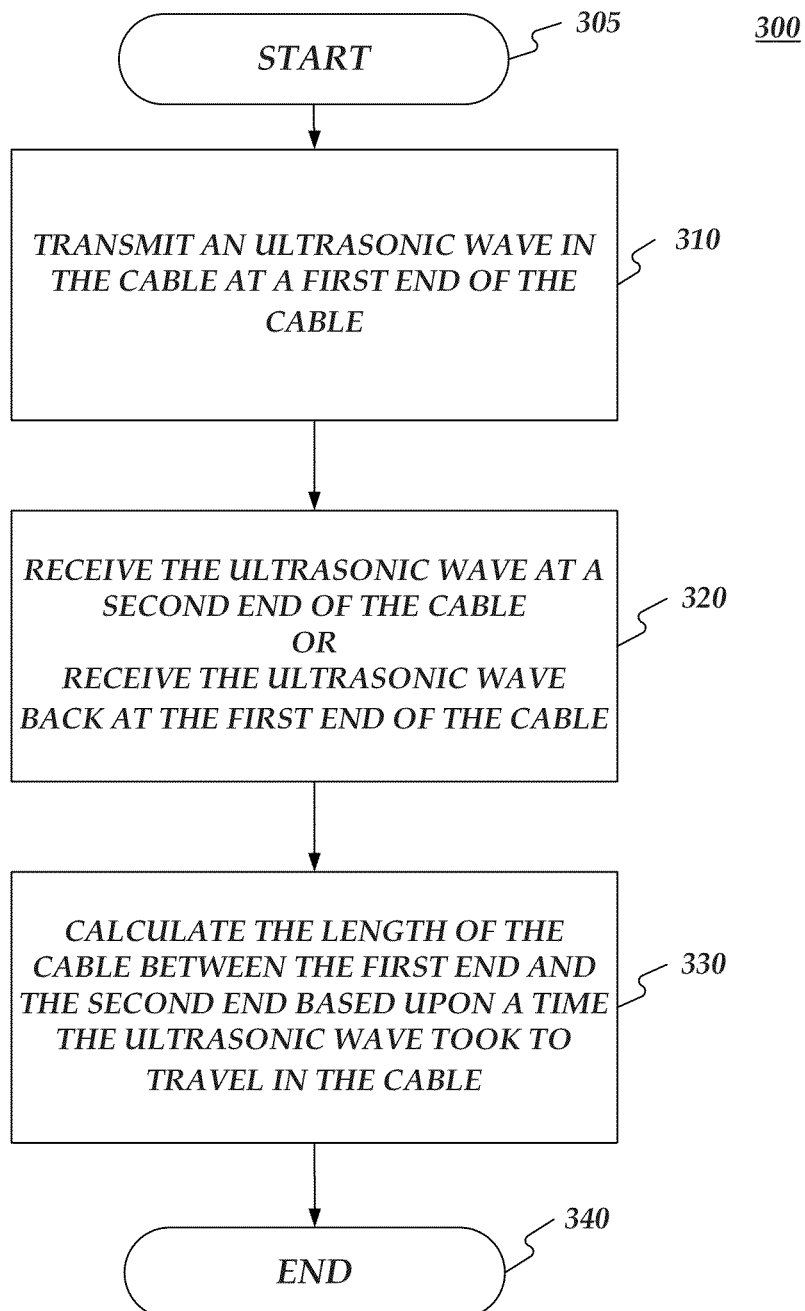
FIG. 3 is a flow chart of a method for measuring a length of a cable.

FIG. 3 is a flow chart setting forth the general stages involved in a method 300 consistent with an embodiment of the invention for measuring a length of a cable. Method 300 may be implemented, for example, using cable measurement device 105 or cable measurement device 205 as described in more detail above with respect to FIG. 1 and FIG. 2. Ways to implement the stages of method 300 will be described in greater detail below. Method 300 may begin at starting block 305 and proceed to stage 310 where a transmitter may transmit an ultrasonic wave in the cable at a first end of the cable. For example, as illustrated in FIG. 1, cable measurement device 105 may be configured to use transmitter 110 to transmit the first signal onto first end 120 of the cable. In other embodiments, cable measurement device 205 may be configured to use transceiver 210 to transmit the second signal onto first end 220 of the cable as shown in FIG. 2.

From stage 310, where transmitter 110 (or transceiver 210) may transmit the ultrasonic wave in the cable at first end 120 or 220 of the cable, method 300 may advance to stage 320 where receiver 115 may receive the ultrasonic wave at second end 125 of the cable or transceiver 210 may receive the ultrasonic wave back at first end 220 of the cable. For example, as illustrated in FIG. 1, cable measurement device 105 may be configured to use receiver 115 to receive the first signal at second end 125 of the cable. In other embodiments, cable measurement device 205 may be configured to use transceiver 210 to receive a reflected version of the second signal at first end 220 of the cable. In other words, once transmitted onto the cable, the second signal may hit second end 225 of the cable and be reflected back to first end 220 from second end 225 of the cable.

After receiver 115 receives the ultrasonic wave at second end 125 of the cable or after transceiver 210 receives the ultrasonic wave back at first end 220 of the cable in stage 320, method 300 may proceed to stage 330 where a component may calculate the length of the cable between the first end and the second end. The component for calculating the length may comprise, but is not limited to, cable measured device 105 or cable measured device 205. The length calculation may be based upon a time the ultrasonic wave took to travel: i) between the first end of the cable and the second end of the cable; or ii) from the first end of the cable to the second end of the cable and back to the first end. For example, consistent with embodiments of the invention, the cable may be swept across to be measured, for example, volumetrically or linearly. In this case, transducers may remain stationery while an electronic scanner ultrasonically scans the whole volume to be measured. A two-dimensional transducers array may transmit these signals (e.g. ultrasonic waves) in a conical fashion diverging from a generation point and impinging onto the volume to be measured. Reflected signals may then be detected by a sensors array and processed to determine the cable's length.

Consistent with the embodiments of the invention, Electromagnetic-acoustic transducers (EMAT) may be used by a cable measurement device (e.g. cable measurement device 105 or cable measurement device 205) to accurately measure the length of a cable. A feature of ultrasonic measurements is the mechanical coupling between the transducer, generally a piezoelectric disk, and the solid, whose properties or structure are to be studied. This coupling may be achieved in one of two ways, for example. In immersion measurements, energy may be coupled between a transducer and a sample by placing them in a tank filled with a fluid, generally water. In contact measurements, the transducer may be pressed directly against the sample, and coupling may be achieved by the presence of a thin fluid layer inserted between the two. When shear waves are to be transmitted, the fluid may be selected to have a significant viscosity.

EMAT may act through a different mechanism than the mechanical coupling described above. When a wire is placed near the surface of an object and is driven by a current at the desired ultrasonic frequency, eddy currents may be induced in a near surface region of the object. If a static magnetic field is also present, these eddy currents may experience Lorentz forces of the form $$F = J \times B$$

where F is a body force per unit volume, J is the induced dynamic current density, and B is the static magnetic induction.

An application of EMATs has been in nondestructive evaluation (NDE) applications such as flaw detection or material property characterization. Couplant free transduction may allows operation without contact at elevated temperatures and in remote locations. The coil and magnet structure can also be designed to excite complex wave patterns and polarizations that may be difficult to realize with fluid coupled piezoelectric probes. In the inference of material properties from precise velocity or attenuation measurements, use of EMATs can eliminate errors associated with couplant variation, particularly in contact measurements.

Consistent with embodiments of the invention, Time Domain Reflectometry (TDR) may be used by cable measurement device 105 or cable measurement device 205 to accurately measure the cable's length. TDR may comprise a measurement technique used to determine the characteristics of electrical lines by observing reflected waveforms. Time-domain transmissometry (TDT) may also be used to measure a transmitted (rather than reflected) impulse or wave.

With TDR, the amplitude of the reflected signal can be determined from the impedance of a discontinuity. The distance to the reflecting impedance can also be determined from the time that a pulse takes to return. A limitation of this process may be the minimum system rise time. The total rise time may comprise, for example, the combined rise time of the driving pulse and that of a device that may monitor the reflections.

The TDR analysis may begin with the propagation of a step or impulse of energy into the cable and the subsequent observation of the energy reflected by the cable. By analyzing the magnitude, duration and shape of the reflected waveform, the nature of the impedance variation in the cable can be determined.

If a pure resistive load is placed on cable measurement device 105 or cable measurement device 205 and a step signal is applied, a step signal may be observed, and its height may be a function of the resistance. The magnitude of the step caused by the resistive load may be expressed as a fraction of the input signal as given by:

$$\rho = \frac{R_L - Z_0}{R_L + Z_0}$$

where $Z_0$ is the characteristic impedance of the cable.

For reactive loads, the observed waveform depends upon the time constant formed by the cable and the characteristic impedance of the cable.

In addition to TDR, Frequency Domain Reflectometry (FDR) may be used. A signal may be launched into a cable and a detector situated at a launch end may pick up both the transmitted swept signal and the signals reflected back from any faults along the way. For example, FDR "looks" into the cable in a similar way as a radio does and "sees" elements between the insertion point and the end.

An FDR-based analysis may use frequency specific pulses first below, then on, and finally above the actual band and frequency used by a radio system. By using pulses of discrete frequencies, a realistic analysis of the cable may be possible. An FDR analysis may be initiated and measurements may be made similar to those in a TDR analysis. Reflections may be measured, elapsed time may be measured, however, in the FDR analysis much more information may be available. By testing with several frequencies, an accurate representation of the cable may be presented to an operator in a very short time. Once the component calculates the length in stage 330, method 300 may then end at stage 340.

Figure 4:
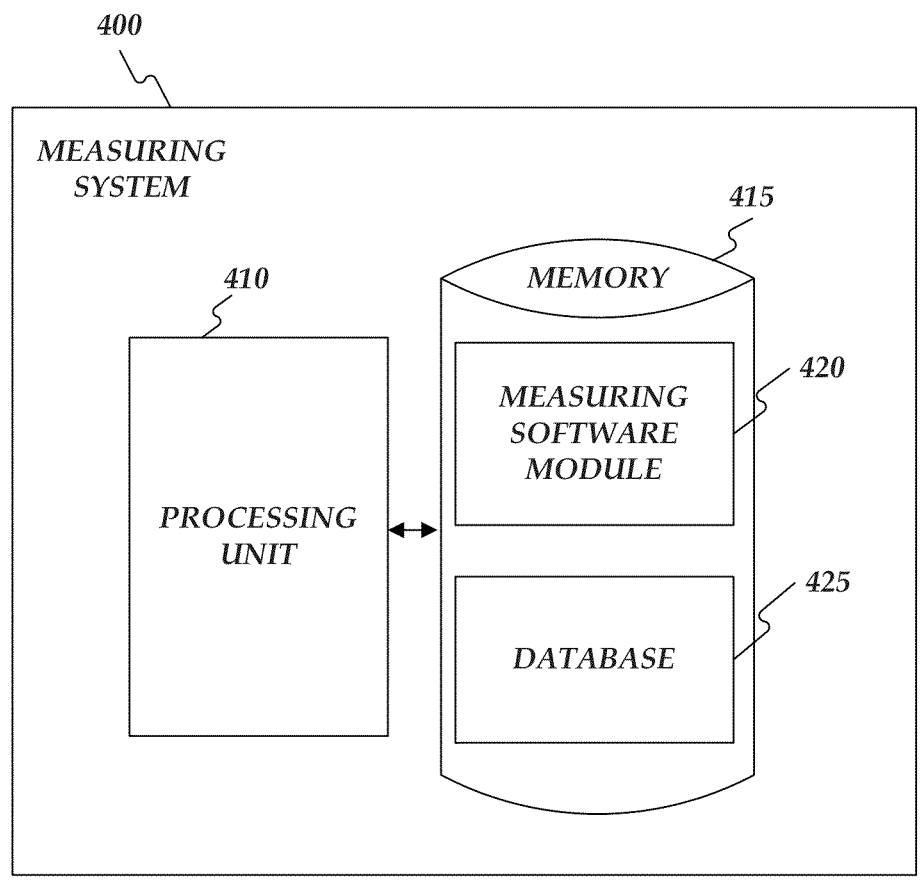
FIG. 4 shows a measuring system.

Cable measurement device 105 or cable measurement device 205, for example, may use a memory, a processing unit (e.g. a microprocessor), and other components to perform the aforementioned cable measurement process (e.g. method 300.) The processing unit may implement program modules to perform the cable measurement process. Program modules may include routines, programs, components, data structures, and other types of structures that perform particular tasks or implement particular abstract data types. For example, FIG. 4 shows a measuring system 400 that may be used by cable measurement device 105 or cable measurement device 205. Measuring system 400 may include a processing unit 410 and a memory 415. Memory 415 may include a measuring software module 420 and a database 425. While executing on processing unit 410, measuring software module 420 may perform, for example, processes for measuring a length of a cable as described in greater detail above with respect to FIG. 3.

Moreover, to perform the aforementioned cable measurement process (e.g. method 300), cable measurement device 105 or cable measurement device 205, for example, may use an electrical circuit comprising discrete electronic elements, packaged or integrated electronic chips containing logic gates, a circuit utilizing a microprocessor, or on a single chip containing electronic elements or microprocessors. In addition, cable measurement device 105 or cable measurement device 205 may use other technologies capable of performing logical operations such as, for example, AND, OR, and NOT, including but not limited to mechanical, optical, fluidic, and quantum technologies to perform the aforementioned cable measurement process.

Embodiment of the present invention may, for example, be implemented using a memory, a processing unit, and other components. Any suitable combination of hardware, software, and/or firmware may be used to implement the memory, processing unit, or other components. The processing unit may implement program modules. Generally, consistent with embodiments of the invention, program modules may include routines, programs, components, data structures, and other types of structures that perform particular tasks or implement particular abstract data types.

Moreover, embodiments of the invention may be practiced with other computer system configurations, including hand-held devices, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present invention may be embodied in hardware and/or in software (including firmware, resident software, micro-code, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present invention are described above with reference to block diagrams and/or operational illustrations of methods, systems, and computer program products according to embodiments of the invention. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

While certain features and embodiments of the invention have been described, other embodiments of the invention may exist. Furthermore, although embodiments of the present invention have been described as being associated with data stored in memory and other storage mediums, aspects can also be stored on or read from other types of computer-readable media, such as secondary storage devices, like hard disks, floppy disks, or a CD-ROM, a carrier wave from the Internet, or other forms of RAM or ROM. Further, the steps of the disclosed methods may be modified in any manner, including by reordering stages and/or inserting or deleting stages, without departing from the principles of the invention.

While certain embodiments of the invention have been described, other embodiments may exist. While the specification includes examples, the invention's scope is indicated by the following claims. Furthermore, while the specification has been described in language specific to structural features and/or methodological acts, the claims are not limited to the features or acts described above. Rather, the specific features and acts described above are disclosed as example for embodiments of the invention.

What is claimed is:

1. A system for measuring a length of a cable, the system comprising:
   a stationary two-dimensional transducer array configured to transmit a plurality of waves in a conical fashion, each of the plurality of waves diverging from a generation point and impinging onto a volume of the cable to be measured;
   a receiver configured to receive the plurality of reflected waves; and
   a component configured to calculate the length of the cable based upon the plurality of reflected waves received at the receiver and to display the calculated length.

2. The system of claim 1, wherein the wave comprises an elastic wave.

3. The system of claim 1, wherein the wave comprises an ultrasonic wave.

4. The system of claim 1, wherein a frequency and wavelength of the wave is optimized to material properties of the cable to minimize attenuation of the wave.

5. The system of claim 1, wherein the stationary two-dimensional transducer array transmitter is further configured to generate the plurality of waves using a vibrating member.

6. The system of claim 1, wherein the component being configured to calculate the length of the cable comprises the component being configured to calculate the length of the cable based upon a conductor type associated with the cable.

7. A system of claim 6, further comprising a user interface configured to receive user input indicating the conductor type.

8. The system of claim 1, wherein the component being configured to calculate the length of the cable comprises the component being configured to calculate the length of the cable based upon based on a conductor type associated with the cable wherein the conductor type comprises one of the following: aluminum conductor steel reinforced (ACSR), all aluminum conductor (AAC), all aluminum alloy conductor (AAAC), medium voltage direct bury cable, high voltage direct bury cable, secondary duplex, and secondary triplex.

9. The system of claim 8, wherein the component being configured to calculate the length of the cable comprises the component being configured to consider material properties of the conductor type associated with the cable.

10. The system of claim 1, wherein the component being configured to calculate the length of the cable comprises the component being configured to calculate the length of the cable based upon one of the following processes: laser interferometers, and holographic interferometers.

11. The system of claim 1, wherein the component being configured to calculate the length of the cable comprises the component being configured to calculate the length of the cable based upon Time-domain transmissometry.

12. The system of claim 1, further comprising a display configured to indicate the calculated length of the cable.

13. A system for measuring a length of a cable, the system comprising:
   a two-dimensional stationary transducer array configured to transmit a plurality of waves in a conical fashion, each of the plurality of waves diverging from a generation point and impinging onto a volume of the cable;
   a stationary sensor array configured to receive the plurality of reflected waves; and
   a component comprising:
   a memory storage; and
   a processing unit coupled to the memory storage, wherein the processing unit is operative to:
   receive cable construction type data,
   calculate the length of the cable based upon the plurality of reflected waves received at the stationary sensor array and the received cable construction type data, and
   display the calculated length.

14. The system of claim 13, further comprising a user interface configured to receive user input indicating the cable construction type data.

15. The system of claim 13, wherein the cable construction type data comprises data indicating one of the following: aluminum conductor steel reinforced (ACSR), all aluminum conductor (AAC), all aluminum alloy conductor (AAAC), medium voltage direct bury cable, high voltage direct bury cable, secondary duplex, and secondary triplex, the component being configured to consider material properties of the conductor type associated with the cable.

16. A method for measuring a length of a cable, the method comprising:

receiving, through a user interface, user input indicating a conductor type associated with the cable, the conductor type indicating how the cable is constructed;

transmitting, by a stationary two-dimensional transducer array, a plurality of waves in a conical fashion, each of the plurality of waves diverging from a generation point and impinging onto a volume of the cable, the plurality of waves, each comprising an ultrasonic wave, a frequency of each of the plurality of waves being optimized to material properties of the cable to minimize attenuation of the wave, the stationary two-dimensional transducer array being configured to generate the wave using a vibrating member;

receiving, by a receiver, the plurality of reflected waves;

calculating the length of the cable between a first end and a second end based upon the plurality of reflected waves received at the receiver, wherein calculating the length of the cable comprises calculating the length of the cable based on the conductor type associated with the cable; and indicating, on a display, the calculated length of the cable.

* * * * *